United States Patent [19]

Falk

[11] 4,435,330

[45] Mar. 6, 1984

[54] PERFLUOROALKYL-ALKYLENE BRANCHED AMPHOTERIC SULFATO BETAINES

[75] Inventor: Robert A. Falk, New City, N.Y.

[73] Assignee: Ciba-Geigy Corporation, Ardsley, N.Y.

[21] Appl. No.: 457,609

[22] Filed: Dec. 29, 1982

[51] Int. Cl.[3] .................... C07C 141/00; C07C 141/02

[52] U.S. Cl. ................................ 260/458 F; 544/158; 546/102; 546/104; 546/172; 546/336; 546/338; 546/339; 546/340; 546/246; 546/247; 546/248

[58] Field of Search ........................ 260/458 F, 458 R; 544/158; 546/102, 104, 172, 336, 338, 339, 340, 246, 247, 248

[56] References Cited

U.S. PATENT DOCUMENTS

| | | | |
|---|---|---|---|
| 4,098,811 | 7/1978 | Falk | 260/458 F |
| 4,209,456 | 6/1980 | Billenstein et al. | 260/458 F |
| 4,381,980 | 5/1983 | Ballschuh et al. | 546/248 |

*Primary Examiner*—Nicky Chan

*Attorney, Agent, or Firm*—Michael W. Glynn

[57] ABSTRACT

Amphoteric branched sulfatobetaines of the formula

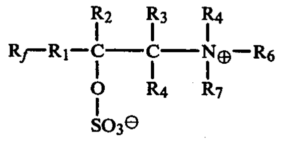

wherein $R_f$ is perfluoroalkyl or perfluoroxyperfluoroalkyl; $R_1$ is a direct bond or a divalent connecting group; $R_2$, $R_3$, and $R_4$ are independently hydrogen or lower alkyl; $R_5$, $R_6$ and $R_7$ are independently lower alkyl, and $R_6$ may additionally represent aralkyl, and $R_6$ and $R_7$ taken together with the nitrogen to which they are attached may also represent piperidino or morpholino and $R_5$, $R_6$ and $R_7$ taken together may also represent pyridyl, acridyl or quinolyl and salts thereof, their preparation and use as surfactants are disclosed.

6 Claims, No Drawings

PERFLUOROALKYL-ALKYLENE BRANCHED AMPHOTERIC SULFATO BETAINES

BACKGROUND OF THE INVENTION

The instant invention relates to novel branched chain sulfatobetaines, their use in reducing the surface tension of aqueous solutions, in the presence or absence of electrolytes, and in rendering cellulosic and natural and synthetic polyamide materials hydrophobic and oleophobic.

It is a further object of the instant invention to provide a simple economic method of preparing such branched chain sulfatobetaines.

Various structural divergent N-type betaines are known, as described in U.S. Pat. No. 4,283,533 and in U.K. Patent Specification No. 1,434,119. However, the structure of these N-type betaines is substantially divergent from those of the instant invention, and the preparation thereof ordinarily entails various cumbersome multistep techniques.

DETAILED DESCRIPTION OF THE INVENTION

The amphoteric branched sulfatobetaines of the instant invention are represented by the formula

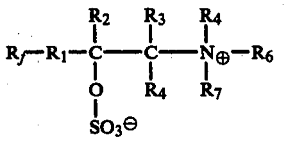

(I)

wherein $R_f$ is straight or branched chain perfluoroalkyl of 3 to 18 carbon atoms, or perfluoroalkoxyperfluoroalkyl of 3 to 18 carbon atoms;

$R_1$ is a direct bond, alkylene of up to 6 carbon atoms, alkyleneoxyalkylene of up to 6 carbon atoms, alkylenethioalkylene of up to 6 carbon atoms, alkyleneoxy of up to 6 carbon atoms, alkenyleneoxyalkylene of up to 6 carbon atoms, alkylenethioalkyleneoxyalkylene of up to 9 carbon atoms, carbonamidoalkylene wherein the alkylene moiety contains up to 6 carbon atoms and the amido nitrogen is further unsubstituted or substituted by lower alkyl, sulfonamidoalkylene wherein the alkylene moiety contains up to 6 carbon atoms and the amido nitrogen is further unsubstituted or substituted by lower alkyl; carbonamidoalkylenethioalkylene wherein the carbonamidoalkylene moiety is as defined hereinabove and the thioalkylene moiety contains up to 6 carbon atoms, or sulfonamidoalkylenethioalkylene wherein the sulfonamidoalkylene moiety is as defined hereinabove and the thioalkylene moiety contains up to 6 carbon atoms;

$R_2$, $R_3$ and $R_4$ are independently hydrogen or lower alkyl;

$R_5$, $R_6$ and $R_7$ are independently lower alkyl, and may additionally represent aralkyl, and $R_6$ and $R_7$ taken together with the nitrogen to which they are attached may also represent piperidino or morpholino, or $R_5$, $R_6$ and $R_7$ taken together with the nitrogen to which they are attached represent pyridyl, acridyl or quinolyl, and salts thereof.

The term "lower", as used hereinabove and hereinafter refers especially to those organic moieties having up to 7 carbon atoms, preferably up to 4 carbon atoms, most preferably methyl or ethyl.

The expression, "aralkyl" as used hereinabove and hereinafter refers especially to those moieties wherein a lower alkyl group is substituted by phenyl or phenyl substituted by lower alkyl or lower alkoxy, preferably phenethyl or benzyl, and most preferably benzyl.

Preferred compounds according to formula I are those wherein $R_f$ is perfluoroalkyl of 3 to 16 carbon atoms. Advantageously the perfluoroalkyl group may be a mixture thereof.

$R_1$ is preferably alkylenethioalkylene of up to 6 carbon atoms, alkylene of up to 6 carbon atoms, or alkylenethioalkyleneoxyalkylene of up to 9 carbon atoms.

$R_2$, $R_3$ and $R_4$ are preferably hydrogen.

$R_5$, $R_6$ and $R_7$ are preferably lower alkyl, and $R_6$ may additionally represent benzyl. More preferably $R_5$, $R_6$ and $R_7$ are methyl or ethyl, and most preferably methyl.

The compounds of formula I are advantageously prepared by reacting an epoxide of the formula

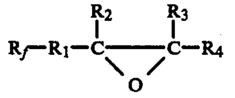

(II)

wherein $R_f$, $R_1$, $R_2$, $R_3$ and $R_4$ are as defined above, with an amine-sulfur trioxide complex of the formula

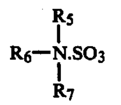

wherein $R_5$, $R_6$ and $R_7$ are as defined above, at a temperature between about 30° C. and 180° C., optionally in the presence of an inert solvent, such as toluene, petroleum ether, dimethylformamide, dimethylsulfoxide, sulfolane, tetrahydrofuran, N-methylpyrrolidine or the like.

The epoxides of formula II are known, or can be prepared in a known manner by conventional techniques. Thus, for example, representative compounds of the formula

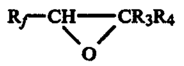

are described in *J. Org. Chem.*, Vol. 21, p. 1328 (1956); representative compounds of the formula

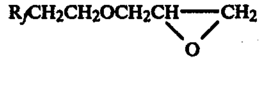

are described in German Offen. No. 2,405,042; and representative compounds of the formula

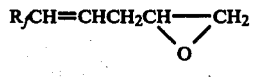

are described in U.S. Pat. No. 4,038,195.

Moreover, the epoxides of formula II can be prepared by dehydrohalogenation of corresponding iodohydrins, e.g. of the formula

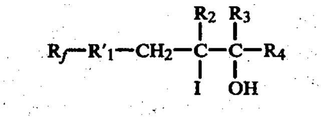

(IV)

wherein $R_1'$ corresponds to $R_1$ minus a methylene group, and $R_f$, $R_2$, $R_3$ and $R_4$ are as defined above, by reaction with an alkaline earth hydroxide at a temperature between about 20° to 80° C. in the presence of an inert solvent, such as a lower alkanol. The compounds of formula IV can be prepared, for example by reacting the corresponding perfluoroalkyl iodide ($R_f$-$R_1'$—I) and the like, with a trialkyl borate, $B(OCR_3R_4CR_2{=}CH_2)_3$, in an inert solvent, such as a lower alkanone, in the presence of a free radical initiator, such as azobisisobutyronitrile at a temperature between about 30° to 80° C. The borate ester, in turn is advantageously prepared by reacting the corresponding allyl alcohol with boric acid in an inert diluent, such as toluene or benzene under azeotropic distillation temperatures to remove the water by-product.

In addition, compounds of formula (II) where $R_1$ contains a thio linking group, can be prepared by reacting a mercaptan of the formula $R_f$-$R_1''$—SH (V)

wherein $R_1''$—S— is the divalent thio containing connecting fragment, which together with —$R_1'''$-, infra, constitutes those —$R_1'$-divalent groups in formula I containing a thio moiety, with a compound of the formula

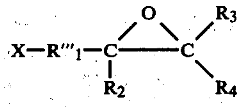

(VI)

where X is halo, preferably chloro, bromo or iodo, $R_1'''$ is a lower alkylene group and $R_2$, $R_3$ and $R_4$ are as defined above, in the presence of a basic agent, such as an alkali metal hydroxide, in an inert solvent, such as tetrahydrofuran, di-lower alkyl ether, and the like, at a temperature between about 20° C. and 100° C.

Moreover, those compounds of formula II containing an oxy linking group can be prepared analogously using the corresponding starting material of the formula $R_f$-$R_1''$—OH as $R_f$ and $R_1''$ are above defined, with the corresponding compound of formula (VI), in like manner.

Also, those compounds, of formula I containing a sulfonamido or carboxamido group in $R_1$ can be prepared by reacting the halo epoxide of formula VI with the corresponding perfluoroalkyl sulfonamide or carboxamide in like manner.

Preferred salts of the compounds of formula I are those salts obtained by reacting the sulfatobetaine with conventional acids and bases, including inorganic mineral acids, such as HCl, $H_2SO_4$, HBr, $H_3PO_4$ and $HNO_3$ lower alkanoic acids, such as acetic acid and proionic acid, lower alkyl sulfonic acids, such as methylsulfonic acid, lower alkyl sulfato acids such as hydrogen methyl sulfate, lower alkyl phosphonic acids such as methylphosphonic acid, and the like. Convention bases include alkali metal and alkaline earth metal hydroxides, bicarbonates, bisulfites and the like, ammonia, lower alkyl amines, such as trimethylamine, ethylamine, etc., and lower alkanol amines, such as ethanolamine and di- or tri-ethanolamine.

Moreover, since the instant compounds are amphoteric, they may form double salts with conventional ionic salts, such as zinc chloride, magnesium sulfate, and the like.

The compounds of formula I and salts thereof are useful in rendering cellulosic and natural and synthetic polyamide materials hydrophobic and oleophobic. The compounds of the instant invention are applied to the substrate in the form of an aqueous solution or emulsion, or if substantially insoluble in water, then dissolved in an organic or aqueous/organic solvent, e.g. methanol, ethanol/water, dichloroethane and the like, and applied to the material by padding, washing or coating the surface thereof. Upon drying, the surface exhibits desirable oil and water repellent properties. Where the compounds of the instant invention are water soluble, per se, then they are useful in reducing the surface tension thereof, and the resultant solutions are useful in cleaning etc. Also, because of their surface tension lowering effects, the instant compounds find use as leveling agents for floor waxes and the like.

EXAMPLE 1

$C_6F_{13}CH_2CH_2SCH_2CH(OSO_3^{\ominus})CH_2N^{\oplus}(CH_3)_3$

To a 100 ml flask was added 3-(1,1,2,2 tetrahydroperfluorooctanethio)-1,2-epoxy propane (30.9 g, 0.7 mole) trimethylamine $SO_3$ complex (14.8 g, 0.11 moles) and N-methylpyrrolidine (50.0 g). The mixture was heated with stirring to 180° C. and maintained at this temperature for five minutes. A clear dark solution resulted which was allowed to cool and was then poured into about 150 mol of toluene. A gummy brown solid was then removed from the solution and was recrystallized repeatedly from isopropanol. The resulting off-white solid was dried in vacuo overnight.

Analysis: Calculated for $C_{14}H_{18}NF_{13}S_2O_4$: C, 29.22; H, 3.15; N, 2.43; F, 42.92; S, 11.15; Found: C, 28.9; H, 3.1; N, 2.4; F, 41.7; S, 11.3.

MMR was consistant with structure: δ 3.28 (11H, S) $—CH_2—N^{\oplus}(CH_3)_3$; δ 2.91 to 4.0 (7H, M) $C_8F_{17}CH_2CH_2SCH_2CH(OSO_3^{-})$.

EXAMPLE 2

$C_8F_{17}CH_2CH_2SCH_2CH(OSO_3^{\ominus})CH_2N^{\oplus}(CH_3)_3$

To a 250 ml flask was added 3-(1,1,2,2 tetradroperfluorodecane thio)-1,2-epoxypropane (40.0 g, 0.075 mole), trimethylamine-sulfur trioxide complex (15.6 g, 0.11 mole) and N-methylpyrrolidine (100.0 g). The mixture was heated with stirring to 180° C. and then held at 160° C. for 30 min. A clear dark solution resulted which separated into two phases upon slow cooling. The top phase was removed and lower phase was washed with isopropanol until it was a gummy brown solid. This solid was dried overnight in vacuo and then recrystallized from absolute ethanol.

Analysis: Calculated for $C_{16}H_{18}NS_2F_{17}$: C, 28.45; H, 2.68; N, 2.07; S, 9.49; F, 47.82; Found: C, 28.2; H, 2.5; N, 1.9; S, 9.4; F, 48.3.

NMR was consistent with structure: δ 3.28 (11H, S) $—CH_2N^{+}(CH_3)_3$; δ 2.91 to 4.0 (7H, M) $C_8F_{17}CH_2CH_2SCH_2CH(OSO^{\ominus}_3)$.

EXAMPLE 3

$C_6F_{13}CH_2CH(OSO_3^-)CH_2N^+(CH_3)_3$

To a two ounce bottle was added 1,1,2,3,3 pentahydroperfluorononylene oxide (10.0 g, 0.027 mole), trimethyl amine.sulfur trioxide complex (4.8 g, 0.035 mole) and N-methylpyrrolidine (10.0 g). The mixture was stirred and heated to 160° C. for 20 minutes in an oil bath. A clear dark solution was obtained. The bottle was allowed to cool below 100° C. and water (10.0 g) was added with stirring. The resulting solution dissolved to give clear solution in water.

EXAMPLE 4

$C_8F_{17}CH_2CH(OSO_3^{\ominus})CH_2N^{\oplus}(CH_3)_3$

To a two ounce bottle was added 1,1,2,3,3 pentahydroperfluoroundecylene oxide (10.0 g, 0.02 mole), trimethylamine sulfur trioxide complex (2.7 g, 0.027 mole) and N-methylpyrrolidine (10.0 g). The mixture was stirred and heated 185° C. for 10 minutes in an oil bath. A clear dark solution was obtained. The bottle was allowed to cool below 100° C. and water (10.0 g) was added with stirring. The resulting solution was water soluble.

EXAMPLE 5

$C_6F_{13}CH_2CH_2SCH_2CH_2CH_2OCH_2C$-
$H(OSO_3^{\ominus})CH_2N^{\oplus}(CH_3)_3$ To a two ounce bottle was added 1-[3-(1,1,2,2,tetrahydroperfluoro-octanethio) propanoxy]-2,3-epoxy propane[1] (10.0 g, 0.019 mole) trimethylamine.sulfur trioxide complex (3.5 g, 0.025 mole) and N-methylpyrrolidine (10.0 g). The mixture was stirred and heated to 160° C. for 20 minutes in an oil bath. A clear dark solution was obtained. The reaction was allowed to cool below 100° C. and water (10.0 g) was added with stirring. The resulting solution was water soluble.

[1]Note: This epoxide is made by the radical addition of allyl glycidyl ether to 1,1,2,2,tetrahydroperfluoro-octanethiol

EXAMPLE 6

Properties of Examples 1-5

Examples 1-5 were tested for textile wetting ability in accordance with the ASTM Draves Method [Draves, C. Am. Dyestuff Rep. 28, 425 (1939)] and for surface tension in distilled water.

| Example | Draves Wetting Speed 0.1%, seconds | Surface Tension 0.01%, dynes/cm |
|---|---|---|
| 1 | 23 | 17.1 |
| 2 | insol. | insol. |
| 3 | 35 | 20.3 |
| 4 | 500 | 24.4 |
| 5 | 37 | 17.3 |

These values indicate that certain shorter chain derivatives have low surface tensions and good wetting characteristics.

What is claimed is:

1. A compound of the formula

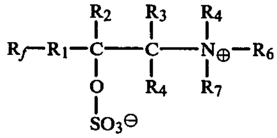

(I)

wherein $R_f$ is straight or branched chain perfluoroalkyl of 3 to 18 carbon atoms, or perfluoroalkoxyperfluoroalkyl of 3 to 18 carbon atoms;

$R_1$ is a direct bond, alkylene of up to 6 carbon atoms, alkyleneoxyalkylene of up to 6 carbon atoms, alkylenethioalkylene of up to 6 carbon atoms, alkyleneoxy of up to 6 carbon atoms, alkenyleneoxyalkylene of up to 6 carbon atoms, alkylenethioalkyleneoxyalkylene of up to 9 carbon atoms, carbonamidoalkylene wherein the alkylene moiety contains up to 6 carbon atoms and the amido nitrogen is further unsubstituted or substituted by lower alkyl, sulfonamidoalkylene wherein the alkylene moiety contains up to 6 carbon atoms and the amido nitrogen is further unsubstituted or substituted by lower alkyl, caronamidoalkylenethioalkylene wherein the carbonamidoalkylene moiety is as defined hereinabove and the thioalkylene moiety contains up to 6 carbon atoms, or sulfonamidoalkylenethioalkylene wherein the sulfonamidoalkylene moiety is as defined hereinabove and the thioalkylene moiety contains up to 6 carbon atoms;

$R_2$, $R_3$ and $R_4$ are independently hydrogen or lower alkyl;

$R_5$, $R_6$ and $R_7$ are independently lower alkyl, and may additionally represent aralkyl, and $R_6$ and $R_7$ taken together with the nitrogen to which they are attached may also represent piperidino or morpholino, or $R_5$, $R_6$ and $R_7$ taken together with the nitrogen to which they are attached represent pyridyl, acridyl or quinolyl, and salts thereof.

2. A compound according to claim 1, wherein $R_f$ is perfluoroalkyl of 3 to 16 carbon atoms.

3. A compound according to claim 2, wherein $R_1$ is alkylenethioalkylene of up to 6 carbon atoms, alkylene of up to 6 carbon atoms, or alkylenethioalkyleneoxyalkylene of up to 9 carbon atoms.

4. A compound according to claim 3, wherein $R_2$, $R_3$ and $R_4$ are hydrogen.

5. A compound according to claim 4, wherein $R_5$, $R_6$ and $R_7$ are lower alkyl.

6. A compound according to claim 5, wherein $R_5$, $R_6$ and $R_7$ are methyl.

* * * * *